United States Patent [19]

Bucher et al.

[11] Patent Number: 4,588,680

[45] Date of Patent: May 13, 1986

[54] ASSAY FOR VIRUSES

[75] Inventors: Doris J. Bucher, New York; Mohamed W. Khan, Flushing, both of N.Y.; Igor G. Kharitonenkov, Moscow, U.S.S.R.

[73] Assignee: Mount Sinai School of Medicine of the City University of New York, New York, N.Y.

[21] Appl. No.: 500,550

[22] PCT Filed: Jul. 31, 1981

[86] PCT No.: PCT/US81/01033

§ 371 Date: Mar. 31, 1983

§ 102(e) Date: Mar. 31, 1983

[87] PCT Pub. No.: WO83/00505

PCT Pub. Date: Feb. 17, 1983

[51] Int. Cl.$^4$ .............. C12Q 1/70; G01N 53/00; G01N 33/545; C12N 9/96
[52] U.S. Cl. ........................... 435/5; 435/7; 435/188; 436/531
[58] Field of Search ............ 435/5, 7, 177, 180, 435/188, 810; 424/86, 85; 436/531

[56] References Cited

U.S. PATENT DOCUMENTS

| | | |
|---|---|---|
| 3,600,494 | 8/1971 | Tomizawa et al. |
| 3,650,437 | 3/1972 | Binnings et al. |
| 3,826,613 | 7/1974 | Parikh et al. ............... 435/5 |
| 4,016,043 | 4/1977 | Schuurs et al. ............ 435/7 |
| 4,195,074 | 3/1980 | Safford, Jr. ............. 435/7 X |
| 4,200,436 | 4/1980 | Mochida et al. ........ 435/7 X |
| 4,292,403 | 9/1981 | Duermeyer .............. 435/5 |

FOREIGN PATENT DOCUMENTS

| | | |
|---|---|---|
| 0038150 | 10/1981 | European Pat. Off. |
| 5071947 | 5/1980 | Japan ....................... 435/7 |
| 1185065 | 3/1970 | United Kingdom . |
| 1503409 | 3/1979 | United Kingdom . |
| 1549069 | 7/1979 | United Kingdom . |

OTHER PUBLICATIONS

Chao, R. K. et al., *The J. of Infectious Diseases*, vol. 139 (4), pp. 483–486, 1979.
Berg, R. A. et al., *The Lancet*, pp. 851–853, 1980.
Yolken, R. H. et al., *The J. of Infectious Diseases*, vol. 142 (4) pp. 516–523, 1980.
Sarkkinen, N. K. et al., *J. of Med. Virology*, vol. 7, 213–220, 1981.
Sarkkinen, N. K. et al., *J. of Clin. Microbiol*, vol. 13 (2), pp. 258–265, 1981.
Harmon, M. W. et al., *J. of Clin. Microbiol*, vol. 15 (1), pp. 5–11, 1982.
Masini K. et al., *J. Immunol Methods*, vol. 36, 173–179 (1980).
Biddison, W. et al., *J. Exper Med*, vol. 146, 690–697, (1977).
Reginster, M. et al., *J. Gen. Virol*, vol. 45, pp. 283–289, 1979.
Joassin, L. et al., *Arch Int Physiol Biochim*, vol. 87(5), pp. 1033–1034, 1979.
Lecomte, J. et al., *J. Virol. Methods*, vol. 2, pp. 211–221, 1981.
D. Bucher "Chromatographic Isolation of the Major Polypeptides of Influenza Virus" in Mahy, B. W. and Barry, R. O. (1975) The Negative Strand Viruses, Acad. Press, London vol. 1, pp. 133–143.
Bucher, D. J. Li, S. S. L, Kehoe, J. M. Kilbourne, E. D., (1976) Proc. Nat. Acad. Sci. USA vol. 73, No. 1, pp. 238–242.
Voller, A., Bidwell, D. E., Bartlett, A., (1976), Bull. World Health Organ., vol. 53.
Bucher, D. J., Kharitonenkov, I. G., Zakomirdin, J. A., Grigoriev, V. B., Klimenko, S. M. and Davis, J. F., (1980) Journal of Virology vol. 36, No. 2, pp. 586–590.
Bucher, D. J., Kharitonenkov, I. G., Lvov, D. K., Pysina, T. V., Lee, H. M. (1980), Intervirology 14: pp. 69–77.
Chem. Abstracts vol. 92, (1980), p. 300 92:177113q.
Oxford, J. S. and Schild, G. C., (1976), Virology 74, pp. 394–402.
Chem. Abstract vol. 94, (1981), p. 333 94:170428d.

*Primary Examiner*—Thomas G. Wiseman
*Assistant Examiner*—Jayme A. Huleatt
*Attorney, Agent, or Firm*—Brumbaugh, Graves, Donohue & Raymond

[57] ABSTRACT

This application discloses a method for assaying viruses in which viral particles or fragments are treated to expose M-protein, and the presence of M-protein is subsequently determined by an immunoassay technique. The M-protein of viruses is quite lipophilic and appears to bind preferentially to surfaces such as polystyrene. This permits the assay to be conducted on a convenient polystyrene or similar solid surface. Detection is preferably by means of an enzyme antibody conjugate.

4 Claims, No Drawings

ASSAY FOR VIRUSES

DESCRIPTION

TECHNICAL FIELD

No simple effective method is currently available for rapidly detecting viruses such as influenza virus in biological fluids. Isolating and identifying viruses from biological specimens typically requires several days to weeks and the usual procedures cannot be readily performed in most clinical laboratories. By the time an infecting viral agent has been identified, its identity tends to be of little more than academic interest to the physician faced with the immediate problem of therapy. The availability of a rapid diagnostic method for influenza viruses (and structurally related viruses) would prevent unnecessary antibiotic therapy in the cases of many infections. Moreover where the patient has been affected with certain viruses, such as influenza type A virus, knowledge of such a fact may indicate treatment with other therapeutic agents such as amantadine.

BACKGROUND ART

Many others are currently interested in developing assay systems which will permit the direct detection of viruses in biological specimens. Most approaches seem to be modeled on the double antibody sandwich similar to that found to be effective for rotavirus detection. For that purpose antirotavirus antibody is adsorbed on a bead of size convenient for handling. The antirotavirus antibody bead is then exposed to a stool specimen suspected of containing rotavirus. Following exhaustive washing of the bead any rotavirus present is "sandwiched" with a second antirotavirus antibody to which enzyme has been conjugated. An enzyme assay is then performed to detect the presence of viral particles.

Nearly all of the reports described assay systems which exploit the double-antibody sandwich (DAS) approach with conjugation of $^{125}I$ or enzyme (alkaline phosphatase, or horseradish peroxidase) to the second antibody, or indirect analysis, which involves the use of a third antibody to which an enzyme or radiolabel has been conjugated. In a limited number of instances competitive inhibition with labelled or quantified antigen has been suggested along with DAS.

The inventors are also aware of one report of direct adsorption of viral antigen to a substrate used to detect intact picornavirus. This approach can be sucessful with picornaviruses if there is no competing protein antigen in the system.

A severe limitation in detecting virus particles through assay for surface antigens is the widespread existence of proteases as in biological specimens. If samples are not immediately frozen and maintained in a frozen state, surface antigens may be degraded and rendered non-reactive with the antibodies intended to detect them.

Two reports of influenza virus detection systems appear in the literature. The first method (Berg et al., 1980) involves a minimum of 24 hours to carry out and uses fluorescent or radioactive substrates to indicate the presence of influenza virus. The procedure is quite complicated and requires special equipment to detect the fluorescence or radioactivity of the indicator. A second approach (Yolken, et al., 1980) employs "capture" antibody on a Microtiter plate to adsorb neuraminidase in intact viral particles. A neuraminidase assay with a fluorescent substrate (methyl umbelliferyl neuraminic acid) indicates the presence of virus. However, the neuraminidase antigen (particularly Nl) varies greatly in its stability as an enzyme among different subtypes. Inactivation of this enzyme prevents analysis. Further limitations associated with this assay are those arising from its dependence on fluorometry (which precludes the use of visual analysis), and the occurrence of non-specific reactions which yield spurious results.

DISCLOSURE OF INVENTION

In accordance with the present invention we have developed a new method for detecting viruses which does not depend on isolating or detecting the viral particle itself, but rather on detecting a major structural protein component of the virion, the M-protein. Use of the M-protein as the detected antigen in a solid phase system for viral assay has a number of advantages. M-protein is a major protein constituent of viruses such as orthomyxoviruses (which include the influenza viruses) paramyxoviruses (which include measles, mumps, parainfluenza and pseudomyxoviruses) and the rhabdoviruses (which include rabies, Marburg and Ebola viruses). The M-protein constitutes approximately 30% of the total viral protein of the virion. Moreover the M-protein is type specific, that is the M-protein of influenza Type A is antigenically distinct from the M-protein of influenza Type B, and both are in turn antigenically distinct from the M-protein of influenza Type C. As a type specific antigen, M-protein is not subject to the seemingly endless antigenic variations to which the hemagglutinin is subject. Thus only one reagent is required to detect all Type A influenza viruses.

Other advantages arise from the fact that the M-protein is very stable. Preparations of M-protein have been boiled and still retain their antigenicity. M-protein has been purified by acidic chloroform: methanol extraction or following solubilization by various detergents and shown to maintain its immunogencity and membrane associating properties. Because the M-protein is situated on the internal side of the lipid envelope of the virion it is protected from adventitious proteases in biological specimens. Thus in carrying out the present assay based on detecting the M-protein, the M-protein can be released from the virion or viral fragment and immediately treated in the assay procedure without loss of sensitivity or reactivity resulting from extraneous proteases which may be present in the biological fluids. Still another advantage of the present invention is that use of the M-protein as the detected protein to assay for the presence of virus does not require that the intact virion be present.

Broadly in carrying out the present invention viral particles or virions are treated to release M-protein contained therein, the M-protein is adsorbed onto a surface which preferentially adsorbs it. Thereafter the presence of the M-protein on the surface is detected by the means of anti-M antibody. In principle, detection of the M-protein may be effected by an anti-M antibody which has been conjugated with an appropriate indicator such as a fluorescent indicator, a radioactive indicator or an enzyme. We prefer, however, to use indirect detection. In indirect detection the surface with adsorbed M-protein is first treated with M antibody, which becomes immunoadsorbed to the M-protein held by the surface. The M antibody is then detected by means of a second antibody to the Fab portion of the M antibody which is conjugated to an indicator. For maximum sensitivity, we generally prefer to use an antibody/enzyme conjugate. We have found that such conjugates are not only generally more sensitive, but moreover yield a result which can be readily measured in a spectrophotometer such as is commonly available in most laboratories.

Because each of the steps in the foregoing process occur rapidly, the complete assay can be normally carried out in a matter of a few hours and we have found that it is generally able to detect as little as 2 ng of the M-protein or about 5 ng of the virus to be assayed.

In more detail the present invention is carried out as follows:

DISPERSION AND ADSORPTION OF M-PROTEIN

As is generally known, viral particles can be disrupted to expose interior contents by incubation in the absence of extraneous proteins for periods of time of 30 minutes up to several hours and at temperatures ranging from room temperature up to 100° C. For release of M-protein and the optimal adhesion thereof to surface, it is generally desired to have a small amount of detergent present. We have found that an anionic detergent such as sodium dodecyl sulfate (SDS) or N-lauroylsarcosine, sodium salt, (Sarkosyl) are particularly suitable. Other anionic surfactants which we would expect to be useful include the common alkalai metal salts of fatty acids or the alkalai metal salts of the allyl or aralkyl sulfates or allyl or aralkyl sulfonates having from about 8 to 18 carbon atoms. We believe that nonionic and cationic detergents may also be useful although greater concentrations of such detergents appear to be necessary to obtain optimal results.

The M (matrix or membrane) protein is a major protein constituent of the envelope of viruses such as the orthomyxoviruses, paramyxoviruses and rhabdoviruses. The polypeptides of these viruses are hydrophobic in nature and highly aggregating. Agents such as urea guanidine hydrochloride in appropriate concentration are known to disrupt the viral particle or fragment to expose the M-protein. Various detergents are also believed to permit the solubilization of the viral polypeptides (such as M-protein, or protein fragments having exposed M-protein) by forming hydrophilic shells around them. Still other known methods for releasing M-protein include acidic chloroform-methanol or creatine ether extraction to disrupt the lipid envelope of the virus.

M-protein will spontaneously adhere to many surfaces preferentially to competing proteins. Presumably this is because of its hydrophobic nature. Utilizing the property we can carry out the assay of this invention by providing for a suitable assay surface which can be conveniently manipulated to which the M-protein will adhere. For instance, we have found that polystyrene will absorb M-protein rapidly (within a few minutes) even with a 10,000 fold excess of competing protein molecules (0.5 $\mu$g/ml of M-protein in 5 mg/ml of bovine serum albumin). This assay takes advantage of this characteristic of the M-protein. We hypothesize that this is related to the hydrophobic nature of M-protein relative to many other polypeptides. This suggests that other hydrophobic surfaces will also be suitable, for instance polyacrylate, polyamide and polyvinyl surfaces.

The surface can be in any suitable form, such as a well in which the assay can be performed so long as it can be conveniently manipulated in the various steps of our assay. We have found 6 mm polystyrene beads to be convenient. When using such beads, the incubation is preferably carried out in glass tubes to avoid competitive adsorption as between the polystyrene pellet which is used for the assay and the surface of the incubation vessel.

In dispersing and adsorbing the M-protein, the amount of detergent used must strike a balance between that which is sufficient to disperse the M-protein, and that which will prevent its adherence to the assay surface. The optional amount obviously depends, inter alia, on the characteristics of the detergent.

The optimal level of detergent also appears to be dependent on the amount of other proteins which are also present in the sample being assayed. Biological samples normally contain small but variable amounts of protein. Moreover, when sampling viruses, it is common to stabilize the sample by adding protein to supress spontaneous fragmentation of the viral particles. Accordingly we prefer in the practice of our procedure to add a substantial amount of protein or protein hydrolysate to the sample along with the detergent in such proportions that the detergent to added protein ratio is optimal for adsorption of M-protein by the surface. In this manner the smaller amounts of adventitious protein present in the sample do not contribute greatly to varying results. Examples of added protein which are useful in the present invention are bovine serum albumin (BSA), allantoic fluid, and veal infusion broth. Others which would be expected to be useful include gelatin and fetal calf serum. Depending on the selection of detergent and added protein, the detergent concentration in the incubation medium may be up to 0.1% and the protein or protein hydrolysate may be up to 10 milligrams/ml. Optimal conditions we have found include incubation using 0.03% Sarkosyl in the presence of 0.1 mg/ml BSA and 0.1% Sarkosyl in the presence of 0.7 mg/ml allantoic fluid.

We generally prefer to disperse the viral proteins by incubating viral fragments or virions in phosphate buffered saline (having a pH of 7.4), or a carbonate buffer having a pH of approximately 9.7. A typical carbonate buffer, described by Voller et al in Bulletin of the World Health Organization, Volume 53 (1976) contains 1.59 grams of sodium carbonate, 2.93 grams of sodium bicarbonate, 0.2 grams of sodium azide and 1,000 ml. of distilled water.

While the sample suspected to contain virus can be a biological fluid directly obtained from the patient such as throat or nasal washings, it is helpful sometimes to prepare the sample by centrifugation before it is treated, for instance, at 1,500 rpm for 15 minutes for clarification or as much as 30,000 rpm for 60 minutes to form an enriched pellet containing viral particle fragments.

In carrying out the dispersion and adsorption of the M-protein, the incubation is continued for a perior of at least 30 minutes and at temperatures which may range from room temperature up to 100° C. For purposes of standardization, we generally prefer to incubate the virus to be assayed in a carbonate buffer solution employing 0.03 Sarkosyl and 0.01% bovine serum albumin at a temperature of 56°, the incubation being continued for a period of $\frac{1}{2}$ to 1 hour.

In reaching the preferred conditions, we have studied the rate of uptake of M-protein by polystyrene beads over periods of 30 minutes up to six hours. We have found that the adsorption is very rapid, normally being over 90% complete at the end of 30 minutes and reaching a plateau beyond which further reaction seems not to occur within about 90 to 120 minutes.

POSTCOATING STEP

The assay surface resulting from the dispersion and adsorption step, which now contains adsorbed M-protein is washed several times typically with PBS-Tween, to remove extraneous fluids. We prefer at this point to also incubate the bead in a veal infusion broth:-carbonate buffer solution for time sufficient to thoroughly saturate any remaining reactive sites on the assay surface. Such saturation prevents the surface from subsequently adsorbing proteins such as the M antibody or antibody-indicator conjugates. Adsorption of the antibodies subsequently used to detect and indicate absorbed M-protein can lead to extraneous variations in the background which will obscure reliable detection of the M-proteins which are to be assayed. In our recent studies we have found that incubation in veal broth:carbonate buffer (1:1) for 30 minutes at 37° C. is sufficient to eliminate background variation. After such incubation the surface is again washed to remove extraneous liquids.

REACTION OF THE M ANTISERUM

The assay surface is then incubated against M-antiserum in a medium which will suppress nonspecific adherence of the antibody. As is generally known from other solid phase immunoassay procedures both proteins and various detergents will contribute to such suppression. The medium is also buffered to a pH near 7 to promote antigen/antibody reaction. Physiological pH is commonly used.

For protein to suppress non-specific reaction, we have successfully used allantoic fluid and bovine serum albumin. The detergent is preferably nonionic in view of the known tendency of ionic detergents to denature the antibody. Among possible nonionic detergents which may be suggested are the ethylene oxide condensate of various amines, sorbitans and alcohols. Examples include the alkyl phenoxyethoxy ethanols, sorbitan ethylene oxide condensates, and polyethylene oxide-polypropylene oxide block polymers.

We prefer to use a PBS-Tween mixture to which from 0.1 to 1 mg/ml of BSA or allantoic fluid have been added.

The antiserum is generated in the usual fashion by injecting a convenient species with M-protein and after a suitable incubation period the anti-M serum recovered. We have found rabbit to be a convenient species with which to work. Greatest sensitivity can be obtained using the rabbit antiserum at a 1:50 dilution; however, dilution ratios may vary from 1:50 to 1:2000. In tests of our invention under various incubation conditions we have found that the antibody adsorption by M-protein is about 60% complete within 5 minutes at room temperature incubation. The reaction is not any more efficient at 37° C. By the end of one hour substantial saturation of the available M-protein appears to have occurred.

REACTION WITH ENZYME-ANTIBODY CONJUGATE

The assay surface which has been treated with M antiserum is again washed several times to remove extraneous fluids and incubated with an indicator-antibody conjugate. As previously indicated, we prefer to use an enzyme antibody conjugate. A conjugate of alkaline phosphatase with goat anti-rabbit Fab antibody is commercially available which we have successfully used in our experiments. This commercial conjugate is diluted in an appropriate incubation medium in accordance with the manufacturer's direction. The medium is selected to supress nonspecific adherence in accordance with customary techniques (discussed above). A sufficient quantity is used, depending on the potency indicated by the manufacturer, to react with approximately 0.5 microgram of M antibody. Generally this means that the antibody/enzyme conjugate is used in a dilution ratio between about 1:250 and 1:2000. The incubation medium for the conjugate we have used is PBS-Tween containing 0.5% bovine serum albumin.

SUBSTRATE ASSAY

The assay surface treated with the enzyme-antibody conjugate is removed, washed again and reacted with a substrate for the enzyme. The substrate selected will, of course, depend upon the indicator used in the conjugate. For alkaline phosphatase, the recommended substrate is typically 4-nitrophenyl phosphate tablets (5 mg) which are dissolved in 5 ml of a 10% diethanolamine buffer. The diethanolamine buffer as described in Voller et al (supra) is prepared from 97 ml diethanolamine, 800 ml water, 0.2 grams sodium azide, 1 molar hydrochloric acid in an amount sufficient to yield a pH of 9.8, and sufficient distilled water to make up a solution of 1000 milliliters. Incubation may be carried out for any convenient period of time. We have found that the optical density in the case of the particular system we have used (which is read at 400 nm) is linearly proportional to the incubation time. For purposes of our assay, we have found that an incubation time of 30 minutes at 37° C. is convenient.

PREPARATION OF ANTISERUM TO M-PROTEIN

M-protein is purified by SDS gel chromatography in Bio Gel A-5 m or Sepharose CL-6B following disruption of virus particles in accordance with established methods (i.e. Mahy & Barry, The Negative Strand Viruses, Chap. 9 (pp. 133–143), Academic Press, London, 1975). M-protein has also been purified for use an an immunogen by chromatography in a Tris-HCl-SDS containing buffer on steric exclusion columns by high pressure liquid chromatography.

M-antibody is prepared in the usual manner in a convenient species (e.g. goat, rabbit or layer animal) with an amount of M-protein sufficient to provoke an immogenic response. Typically the host animal is inoculated two or more times at intervals, and the serum is harvested when the anti-M titer has risen to the desired level.

While some immunologic response will be obtained from M-protein as isolated in detergent upon inoculation, we prefer to use a hyperimmune serum having an anti-M titer of at least 1:10,000 prepared by using aggregated M-protein. M-protein is aggregated by removal of the SDS to produce a fine opalescent suspension. The SDS can be removed by continuous ultrafiltration with the Amicon model 56 equipped with PM-10 membranes (Bucher et al., J. Virology 36:2 pp. 586–590, November, 1980) SDS can also be removed from M-protein preparations by exhaustive dialysis of concentrated preparations of M-protein (0.1–10 mg/ml) against large volumes of distilled water at 4° C. Sample may require mild heating on a daily basis to resolubilize some SDS which precipitates in the cold. Rabbits are immunized subcutaneously with 10 μg of aggregated M-protein (prepared as described) in Freund's adjuvant. An additional 10 μg of M-protein is injected intraveneously at the same time. (A control bleeding is taken before any M-protein is administered). After 42 days, the animals are boosted with 10 μg of aggregated M-protein (no Freund's) intravenously. A test bleeding is taken 7 days later. The serum is assayed in the Microtiter assay system as described below with M-protein as an absorbent. If the titer is sufficiently high (in excess of 10,000), the animals are exsanguinated and the serum considered satisfactory for test purposes. If the titer is below 10,000, an additional 10 μg boost is administered and the serum evaluated 7 days later as previously described.

TITRATION OF ANTI-M ANTISERA

Purified M-protein (by SDS gel chromatography) is assayed by the Lowry method for protein concentration. SDS is not removed from this M-protein preparation.

M-protein solution is diluted to contain 0.2-0.4 μg/ml or 20-40 ng in 100 μl. The diluted M-protein (100 μl/well) is added to the wells on a Microtiter plate (Microelisa) and adsorption allowed to proceed overnight at 4°. The following day the plates are washed 3 times with PBS-Tween. Starting at a 1:50-1:100 dilution, twofold dilutions are made on the plate in PBS-Tween containing 0.5% allantoic fluid. Antigen-antibody reaction proceeds overnight at 4°. The following day the plates are washed 3 times with PBS-Tween. A predetermined concentration range (1:250-1:2000) of goat antirabbit Fab conjugated with alkaline phosphatase and diluted in PBS-Tween containing 0.5% BSA is added and incubated overnight at 4°. The following day the plates are washed with PBS-Tween 3 times. One hundred μl of a solution containing 1 mg/ml paranitrophenyl phosphate in 10% diethanolamine buffer is added. Incubation is at room temperature in the dark for 30 minutes. Absorbance is read at 405 nm in the Micro Elisa Reader (Dynatech). Titers are determined by calculation of the reciprocal of the dilution to give a value of 0.3 optical density units.

While the present invention has been particularly described as an assay to detect M-protein in viruses, it will be evident that by appropriate modification of technique the invention may equally be utilized as an assay for antibodies to M-protein. In this modification M-protein is prepared as described above, for instance, in the procedure for measuring the titer of anti-M serum. A predetermined quantity of M-protein is then used to saturate the assay surface and the assay surfaces thus treated and incubated against various dilutions of serum suspected to contain M-antiserum. The titer of the M-antibody contained in the serum being assayed is then determined, for instance by the ELISA detection procedure described above. If this modification is used, for example, to assay patients' sera for M-antibody, it will be obvious that the enzyme immunoglobulin to which the enzymes is linked will be an antibody to the Fab portion of human M-antibody.

EXAMPLE 1

A sample containing influenza virus is incubated in a glass tube containing 0.3 ml of carbonate buffer in which 0.03% Sarkosyl and 0.01% bovine serum albumin are dissolved. A six millimeter diameter polystyrene bead with a specular finish is placed in this incubation medium.

After incubation for one hour at 56° C. the bead is removed and washed three times with phosphate buffered saline-Tween solution.

The washed bead is then incubated in a veal infusion broth:carbonate buffer (1:1) for 30 minutes at 37° C. As indicated above, this incubation is optional but is desirable because it eliminates background variation by saturating unreacted sites on the polystyrene bead.

After incubation in the veal infusion broth, the bead is washed again three times and placed in a new tube where it is incubated for one hour with rabbit anti-M serum diluted in PBS-Tween containing 0.5% allantoic fluid diluted in a 1:50 ratio. The bead is washed again after this incubation step and incubated for a further hour at 37° C. with goat antibody to rabbit Fab conjugated with alkaline phosphatase. The conjugate is diluted in PBS-Tween containing 0.5% BSA.

After incubation with the enzyme-antibody conjugate the bead is removed, washed again three times with 0.3 ml of PBS-Tween and placed in a new tube where it is incubated with 4-nitrophenyl phosphate substrate in a 10% diethanolamine buffer solution. After incubation for 30 minutes at 37° C. the reaction is stopped by adding 0.5 ml of 1 molar sodium hydroxide. Thereupon the absorbance of the solution is read at 400 nm.

EXAMPLE 2

Influenza viruses were harvested from the allantoic fluid of embryonated eggs. The samples were clarified by low speed centrifugation at 1500 rpm. to remove extraneous debris. The supernatant was further centrifuged at 30,000 rpm for 30 minutes, the resulting pellet was redispersed in 0.3 ml of 0.03% Sarkosyl in carbonate buffer. A polystyrene bead was added and the sample heated at 56° C. for 30 minutes.

The bead was removed and washed three times in PBS-Tween. It was then treated with veal infusion broth: carbonate buffer (1:1) for 30 minutes at 37° C. The bead was removed, washed again three times with PBS-Tween, and transferred to a new tube.

Rabbit M-antiserum at a 1:200 dilution was added and the bead incubated for one hr. at room temperature. The bead was removed again, washed three times in PBS-Tween and transferred to a fresh tube. Goat antirabbit Fab antibodies conjugated with alkaline phosphate (dilution 1:250) were added and incubated for 1 hr. at 37° C.

The bead was removed from the incubation medium, washed three times with PBS-Tween and transferred to a new tube in which the phosphatase enzyme assay was performed at 37° C. for 30 minutes.

EXAMPLE 3

Following generally the procedure of Example 2, virus can be assayed directly in allantoic fluid by the addition of 0.15 ml of 0.06% Sarkosyl to 0.15 ml allantoic fluid containing influenza virus (final concentration of Sarkosyl is 0.03%). Both centrifugation steps in this case are omitted. The polystyrene pellet is added and incubated for 30 minutes at 56° C.

The pellet to which M-protein has been absorbed is then removed and treated in the veal infusion broth: carbonate buffer and the remaining steps of the procedure as described in Example 2.

EXAMPLE 4

In still another modification, virus in veal infusion broth is diluted 1:1 with carbonate buffer containing 0.06% Sarkosyl (final concentration is 0.03%). 0.3 ml of this mixture is then placed in a glass incubation vessel together with a 6 mm polystyrene bead and incubated 30 minutes at 56° C. The bead is removed, washed three times with PBS-Tween and then incubated with rabbit M-antiserum for one hour at room temperature at a dilution of 1:200. The assay is then completed as described in the remaining steps of Example 2. In this modification, both the centrifugation steps and the post-coating steps described in Example 2 are omitted.

We claim:

1. A method for detecting viruses having M-protein in virion, comprising the steps of:
   (a) incubating the sample suspected to contain said virus at a temperature of about 20° C. to about 100° C. for at least 1 minute in the presence of an assay surface which preferentially adsorbs M-proteins or viral fragments having exposed M-protein and an incubation medium effective to disrupt viral particles and release M-protein or viral fragments containing exposed M-protein, whereby said M-protein or viral fragments are adsorbed on said surface;
   (b) incubating the surface having M-protein adsorbed thereon with an M antibody which is specific for the M-protein of the virus to be assayed in an incubation medium which suppresses non-specific adherence of the antibody; and
   (c) thereafter detecting the extent to which the M antibody has been immunoadsorbed by proteins adhering to said surface.

2. The method according to claim 1 wherein said M antibody which is immunoadsorbed by M-protein on the surface is detected by treating the surface to which M antibody is adsorbed with a second antibody which is immunoadsorbed by the Fab portion of the M antibody, the second antibody being conjugated with an indicator, and thereafter assaying for said indicator.

3. A method according to claim 2 wherein said indicator is an enzyme.

4. A method according to claims 1, 2 or 3 wherein said surface to which proteins have been adsorbed in step (a) is further treated prior to step (b) by incubation with a protein or protein hydrolysate to which M antibody is non-reactive, which protein or hydrolysate will be effective to saturate unreacted protein adsorbing sites on the surface.

* * * * *